US010603384B2

(12) United States Patent
Paulus et al.

(10) Patent No.: US 10,603,384 B2
(45) Date of Patent: Mar. 31, 2020

(54) PHARMACEUTICAL COMPOSITION CONTAINING AN ANTIVIRALLY ACTIVE DIHYDROQUINAZOLINE DERIVATIVE

(71) Applicant: AICURIS GMBH & CO. KG, Wuppertal (DE)

(72) Inventors: Kerstin Paulus, Ratingen (DE); Wilfried Schwab, Velbert (DE); Dominique Grunder, Belp (CH); Peter Van Hoogevest, Neustadt an der Weinstrasse (DE)

(73) Assignee: AICURIS GMBH & CO. KG, Wuppertal (DE)

( * ) Notice: Subject to any disclaimer, the term of this patent is extended or adjusted under 35 U.S.C. 154(b) by 0 days.

(21) Appl. No.: 14/381,290

(22) PCT Filed: Feb. 28, 2013

(86) PCT No.: PCT/EP2013/054114
§ 371 (c)(1),
(2) Date: Aug. 27, 2014

(87) PCT Pub. No.: WO2013/127970
PCT Pub. Date: Sep. 6, 2013

(65) Prior Publication Data
US 2015/0133461 A1    May 14, 2015

(30) Foreign Application Priority Data
Feb. 29, 2012 (DE) .................. 10 2012 101 680

(51) Int. Cl.
*A61K 47/40* (2006.01)
*A61K 9/00* (2006.01)
*A61K 47/18* (2017.01)
*A61K 31/517* (2006.01)
*A61K 9/08* (2006.01)
*C07D 239/84* (2006.01)
*A61K 47/02* (2006.01)
*A61K 47/26* (2006.01)

(52) U.S. Cl.
CPC ............ *A61K 47/40* (2013.01); *A61K 9/0019* (2013.01); *A61K 9/08* (2013.01); *A61K 31/517* (2013.01); *A61K 47/02* (2013.01); *A61K 47/183* (2013.01); *A61K 47/26* (2013.01); *C07D 239/84* (2013.01)

(58) Field of Classification Search
CPC .... A61K 31/517; A61K 47/02; A61K 47/183; A61K 47/26; A61K 47/40; A61K 9/0019; A61K 9/08; C07D 239/84
See application file for complete search history.

(56) References Cited

U.S. PATENT DOCUMENTS

| 7,196,086 | B2 | 3/2007 | Wunberg et al. |
| 8,084,604 | B2 | 12/2011 | Goossen et al. |
| 8,372,972 | B2 | 2/2013 | Goossen et al. |
| 8,513,255 | B2 | 8/2013 | Wunberg et al. |
| 2005/0065160 | A1 | 3/2005 | Wunberg et al. |
| 2007/0191387 | A1 | 8/2007 | Wunberg et al. |
| 2009/0221822 | A1 | 9/2009 | Goossen et al. |
| 2012/0130072 | A1 | 5/2012 | Goossen et al. |
| 2013/0066073 | A1 | 3/2013 | Goossen et al. |

FOREIGN PATENT DOCUMENTS

| PT | 1622880 E | 6/2007 |
| WO | 01/91751 A1 | 12/2001 |
| WO | 2006133822 A1 | 12/2006 |

OTHER PUBLICATIONS

Strickley et al, Pharmaceutical Research, vol. 21, No. 2, Feb. 2004 pp. 201-230.*
International Search Report from PCT/EP2013/054114 dated Apr. 5, 2013.
Thorsteinn Loftsson, "What are cyclodextrins?", (3 pages), http://eurocdsoc.com. (2009).
"Cavitron and Cavasol hydroxypropyl-B-cyclodextrins: Product Overview", Ashland Product Brochure (2009) (4 pages).
Baumann et al., "Pharmacokinetics, metabolism and distribution of PEGs and PEGylated proteins: quo vadis?," Drug Discovery Today, vol. 19, No. 10, pp. 1623-1631 (Oct. 2014).
Brewster et al., "The potential use of cyclodextrins in parenteral formulations," Jour. Parenteral Sci. & Tech., Vo. 43, No. 5, pp. 231-240 (Sep.-Oct. 1989).
Brewster et al., "Cyclodextrins as pharmaceutical solubilzers," Adv. Drug Delivery Rev., 59, pp. 645-666 (2007).
Cagno et al., "ß-Cyclodextrin-dextran polymers for the solubilization of poorly soluble drugs," Intl. J. Pharmaceutics, 468, pp. 258-263 (2014).
Carpenter et al., "Safety of Parenteral Hydroxypropyl ß-Cyclodextrin," J. of Pharm. Sci., vol. 84, No. 2, pp. 222-225 (Feb. 1995).
Duchêne et al., "Thirty years with cyclodextrins," Intl. J. Pharmaceutics, 514, pp. 58-72 (2016).
European Medicines Agency, "Cyclodextrins used as excipients," EMA/CHMP/333892/2013, pp. 1-16 (Oct. 9, 2017).
Gidwani et al., "A Comprehensive Review on Cyclodextrin-Based Carriers for Delivery of Chemotherapeutic Cytotoxic Anticancer Drugs," BioMed Res. Intl., vol. 2015, Article ID 198268, pp. 1-15 (2015).

(Continued)

*Primary Examiner* — Jean P Cornet
(74) *Attorney, Agent, or Firm* — Millen White Zelano & Branigan, PC

(57) ABSTRACT

The invention relates to pharmaceutical compositions, particularly for intravenous administration, containing {8-fluoro-2-[4-(3-methoxyphenyl)piperazine-1-yl]-3-[2-methoxy-5-(trifluoromethyl)phenyl]-3,4-dihydroquinazoline-4-yl}acetic acid in combination with at least one of the cyclodextrin excipients, lysine and arginine; the method for its production; and its use in methods of treatment of and/or as a prophylactic for illnesses, particularly its use as an antiviral, preferably against cytomegaloviruses.

44 Claims, No Drawings

(56) References Cited

OTHER PUBLICATIONS

Li et al., "Comparison in toxicity and solubilizing capacity of hydroxypropyl-ß-cyclodextrin with different degree of substitution," Intl. J. Pharmaceutics, 513, pp. 347-356 (2016).

Gullapalli et al., "Polyethylene glycols in oral and parenteral formulations—A critical review," Intl. J. Pharmaceutics, 496, pp. 219-239 (2015).

Hermansky et al., "Effects of Polyethylene Glycol 400 (PEG 400) Following 13 Weeks of Gavage Treatment in Fischer-344 Rats," Fd Chem. Toxic, vol. 33, No. 2, pp. 139-149 (1995).

Jambhekar et al., "Cyclodextrins in Pharmacy: Background and Introduction," JChrDD, vol. 4, Issue 1, pp. 14 (2013).

Jambhekar et al., "Cyclodextrins in pharmaceutical formulations II: solubilization, binding constant, and complexation efficiency," Drug Discovery Today, Vo. 21, No. 2, pp. 363-368 (Feb. 2016).

Jang et al., "Safety Evaluation of Polyethylene Glycol (PEG) Compounds for Cosmetic Use," Toxicol. Res., Vo. 31, No. 2, pp. 105-136 (2015).

Jansook et al., "Cyclodextrins: structure, physicochemical properties and pharmaceutical applications," Intl. J. Pharmaceutics, 535, pp. 272-284 (2018).

Kantner et al., "Long-Term Parenteral Administration of 2-Hydroxypropyl-ß-Cyclodextrin Causes Bone Loss," Toxicologic Pathology, 40, pp. 742-750 (2012).

Kurkov et al., "Cyclodextrins," Intl. J. Pharmaceutics, 453, pp. 167-180 (2013).

Li et al., "Systemic toxicity and toxicokinetics of a high dose of polyethylene glycol 400 in dogs following intravenous injection, " Drug and Chem. Toxic., 34(2), pp. 208-212 (2011).

Mayur et al., "Cyclodextrin in Drug Delivery: A Review," RRJPPS, vol. 1, Issue 1, pp. 19-29 (2012).

Montaguti et al., "Acute Intravenous Toxicity of Dimethyl Sulfoxide, Polyethylene Glycol 400, Dimethylformamide, Absolute Ethanol, and Benzyl Alcohol in Inbred Mouse Strains," Arzneim.-Forsch/Drug Res., 44(1), No. 4, pp. 566-570 (1994).

Soakham et al., "γ-Cyclodextrin," Intl. J. Pharmaceutics, 516, pp. 278-292 (2017).

Shrimpi et al., "Cylodextrins: Application in different routes of drug administration," Acta Pharm. 55, pp. 139-156 (2005).

Szejtli, "Past, present, and future of cyclodextrin research," Pure Appl. Chem., vol. 76, No. 10, pp. 1825-1845 (2004).

Malanga et al.: Journal of Pharmaceutical Sciences 105 (2016) 2921-2931.

Rasheed et al; "Cyclodextrins as drug carrier molecule; A review" Scipharm.2008.76.567 -.

* cited by examiner

PHARMACEUTICAL COMPOSITION CONTAINING AN ANTIVIRALLY ACTIVE DIHYDROQUINAZOLINE DERIVATIVE

The present invention relates to a pharmaceutical composition, containing {8-fluoro-2-[4-(3-methoxyphenyl)piperazine-1-yl]-3-[2-methoxy-5-(trifluoromethyl)phenyl]-3,4-dihydroquinazoline-4-yl}acetic acid or a salt, a solvate or a solvate of a salt thereof.

The invention further relates to methods for the production and use of the composition in methods of treatment and/or prevention of virus infections, as well as its use for the production of medicinal drugs for use in treating and/or preventing virus infections, in particular for use in treating infections with the human cytomegalovirus (HCMV) or another representative of the Herpes viridae group.

{8-fluoro-2-[4-(3-methoxyphenyl)piperazine-1-yl]-3-[2-methoxy-5-(trifluoromethyl)phenyl]-3,4-dihydroquinazoline-4-yl}acetic acid is known, for example, from WO 2004/096778, full disclosure of which is included herein by reference; it was developed by Applicant as a promising candidate for an antivirally active substance, in particular for combating infections caused by the human cytomegalovirus. However, in the course of development it was discovered that problems occurred with the solubility of the substance, and in particular it proved complicated to produce stable formulations for intravenous administration or solid easily soluble compositions for producing solutions used for intravenous administration.

It is thus an object of the invention to describe a pharmaceutical composition that is used in particular for intravenous administration, that contains {8-fluoro-2-[4-(3-methoxyphenyl)piperazine-1-yl]-3-[2-methoxy-5-(trifluoromethyl)phenyl]-3,4-dihydroquinazoline-4-yl}acetic acid, that has long-term stability and can be stored, and that in addition has a substantially physiological pH.

A further object of the invention is to describe a pharmaceutical composition with which it is possible, in a simple and reliable manner, to produce pharmaceutical compositions for intravenous administration which contain {8-fluoro-2-[4-(3-methoxyphenyl)piperazine-1-yl]-3-[2-methoxy-5-(trifluoromethyl)phenyl]-3,4-dihydroquinazoline-4-yl}acetic acid and which also remain stable for an adequate period of time, e.g. more than 24 hours.

Within the scope of the invention the term "stability" is understood to mean not only the chemical stability of the constituents of the pharmaceutical composition, but also the stability of the solution itself. In particular, the composition according to the invention must be stable against precipitation of the constituents.

In this context, the term "stability" means that at 2° C. to 8° C., or at 25° C. or at 40° C. the pharmaceutical compositions according to the invention contain a minimum proportion of >90% and preferably >95% {8-fluoro-2-[4-(3-methoxyphenyl)piperazine-1-yl]-3-[2-methoxy-5-(trifluoromethyl)phenyl]-3,4-dihydroquinazoline-4-yl}acetic acid for a storage period of at least two, preferably at least three, and most preferred at least six weeks, when said liquid pharmaceutical compositions are measured using one of the HPLC methods 1-3. Said stability of the liquid pharmaceutical compositions is regarded as adequate within the scope of the invention.

Furthermore, the term "stability" means that, after they have been diluted or reconstituted to a final concentration of 0.8-10 mg/ml for infusion at 2° C. to 8° C., the compositions according to the invention contain a minimum proportion of 90%, preferably at least 95%, of {8-fluoro-2-[4-(3-methoxyphenyl)piperazine-1-yl]-3-[2-methoxy-5-(trifluoromethyl)phenyl]-3,4-dihydroquinazoline-4-yl}acetic acid for a period of at least four hours, preferably at least six hours, and most preferred at least 24 hours in storage when, after dilution or reconstitution, said liquid pharmaceutical compositions are measured using one of the HPLC methods 1-3. Said stability of the pharmaceutical compositions after dilution or reconstitution is regarded as adequate within the scope of the invention.

It has surprisingly been discovered that pharmaceutical compositions, in particular those used for intravenous administration, that contain {8-fluoro-2-[4-(3-methoxyphenyl)piperazine-1-yl]-3-[2-methoxy-5-(trifluoromethyl)phenyl]-3,4-dihydroquinazoline-4-yl}acetic acid as well as water can be stabilized by adding at least one excipient selected from cyclodextrins, lysine and arginine. It has further been discovered that such compositions can be lyophilized in order to obtain a stable, solid pharmaceutical composition that can be reconstituted in a simple manner for injection purposes, e.g. by adding water, as a result of which, in turn, a stable pharmaceutical composition, e.g. for intravenous administration, can be obtained.

The subject matter of the invention are thus pharmaceutical compositions, in particular for intravenous administration, that possess the following constituents, namely:
a) {8-fluoro-2-[4-(3-methoxyphenyl)piperazine-1-yl]-3-[2-methoxy-5-(trifluoromethyl)phenyl]-3,4-dihydroquinazoline-4-yl}acetic acid or a salt, a solvate or a solvate of a salt thereof,
b) at least one excipient selected from the cyclodextrins, lysine and arginine, and
c) water.

In addition, subject matter of the invention are pharmaceutical compositions which are produced by lyophilization of the above-mentioned pharmaceutical composition.

Within the scope of the invention, the term "salts" is understood to mean physiologically acceptable salts of {8-fluoro-2-[4-(3-methoxyphenyl)piperazine-1-yl]-3-[2-methoxy-5-(trifluoromethyl)phenyl]-3,4-dihydroquinazoline-4-yl}acetic acid. Physiologically acceptable salts of {8-fluoro-2-[4-(3-methoxyphenyl)piperazine-1-yl]-3-[2-methoxy-5-(trifluoromethyl)phenyl]-3,4-dihydroquinazoline-4-yl}acetic acid comprise acid addition salts of mineral acids, carbonic acids and sulfonic acids, for example of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of {8-fluoro-2-[4-(3-methoxyphenyl)piperazine-1-yl]-3-[2-methoxy-5-(trifluoromethyl)phenyl]-3,4-dihydroquinazoline-4-yl}acetic acid also comprise salts of usual bases, such as for example and preferably alkali metal salts (e.g. sodium and potassium salts), alkaline earth metal salts (e.g. calcium and magnesium salts), ammonium salts derived from ammonia or organic amines having 1 to 16 C-atoms, such as for example and preferably monoethylamine, diethylamine, triethylamine, ethyldiisopropylamine, monoethanolamine, diethanolamine, triethanolamine, dicyclohexylamine, dimethylaminoethanol, 2-amino-2-methyl-1,3-propanediol, procaine, dibenzylamine, N-methylmorpholine, ethylene diamine and N-methylpiperidine as well as salts of alkaline amino acids.

Within the scope of the invention the term "solvates" refers to those forms of {8-fluoro-2-[4-(3-methoxyphenyl)piperazine-1-yl]-3-[2-methoxy-5-(trifluoromethyl)phenyl]-3,4-dihydroquinazoline-4-yl}acetic acid which form a complex through coordination with solvent molecules. Hydrates are a special form of solvates in which the coordination takes place with water.

As is readily apparent to a person skilled in the art, {8-fluoro-2-[4-(3-methoxyphenyl)piperazine-1-yl]-3-[2-methoxy-5-(trifluoromethyl)phenyl]-3,4-dihydroquinazoline-4-yl}acetic acid possesses a stereocentre at the carbon in the 4-position in the dihydroquinazoline ring. Within the scope of the present invention, it is particularly preferable if this carbon possesses the S-configuration.

A cyclodextrin according to the invention is understood to be any modified or non-modified cyclodextrin. In this case, because of the size of the cavity in the ring, preference is given to β-cyclodextrins and in particular to modified β-cyclodextrins such as, for example, hydroxyalkyl-β-cyclodextrins, e.g. hydroxymethyl-β-cyclodextrin, hydroxyethyl-β-cyclodextrin or hydroxypropyl-β-cyclodextrin, alkyl-hydroxyalkyl-β-cyclodextrins, e.g. methyl-hydroxypropyl-β-cyclodextrins or ethyl-hydroxypropyl-cyclodextrins or sulfoalkyl-cyclodextrins.

Within the scope of the invention, the water used for preparation purposes is normally water that is used for injections.

Within the scope of the present invention the expression "possess" or "possessing" denotes a non-exhaustive enumeration and, along with the explicitly mentioned components or steps, does not exclude any other components or steps.

Within the meaning of the present invention, the expression "consist of" or "consisting of" denotes an exhaustive enumeration and, apart from the explicitly mentioned components or steps, excludes any other components or steps.

Within the scope of the present invention, the expression "consist substantially of" or "consisting substantially of" denotes a partially exhaustive enumeration and denotes methods or compositions which, besides the mentioned components and steps, possess only such other components and steps that do not materially modify the character of the composition or of the method according to the invention, or which are present in quantities that do not materially modify the character of the composition or of the method according to the invention.

If, within the scope of the present invention, a composition or a method is described using the expression "possess" or "possessing", this explicitly includes compositions or methods that consist of the components or steps mentioned or that substantially consist of the components or steps mentioned.

Within the framework of the invention it is preferred if the pharmaceutical composition according to invention further possesses at least one buffer that is preferably selected from the phosphate buffers, the Tris buffers and the citrate buffers.

By adding the buffer it can, in particular, be ensured that the composition always possesses a physiological pH. The buffers named are preferred, in particular due to the fact that they are well tolerated.

It is further preferable, within the scope of the invention, if the pharmaceutical composition according to the invention further possesses at least one sugar, preferably selected from the group consisting of glucose, sucrose, lactose, maltose, trehalose, sorbitol and mannitol.

It has been found that the pharmaceutical composition according to the invention can again be significantly stabilized by adding a sugar, and in particular one of the sugars explicitly mentioned above. Furthermore, it has been found that the addition of a sugar can facilitate the production of a solid composition by lyophilization, as well as renewed reconstitution of such a solid composition in order to produce a pharmaceutical composition in particular for intravenous administration. Also, the addition of the at least one sugar serves to adjust the osmolality of the solution and to suppress any hemolysis that might occur.

Within the scope of the invention it is furthermore preferred that {8-fluoro-2-[4-β-methoxyphenyl)piperazine-1-yl]-3-[2-methoxy-5-(trifluoromethyl)phenyl]-3,4-dihydroquinazoline-4-yl}acetic acid or a salt, a solvate or a solvate of a salt thereof is present in the pharmaceutical composition in an amount corresponding to 1 to 100 mg, preferably 2 to 50 mg, more preferably 2 to 25 mg, and in particular to 5 to 20 mg of pure active compound per ml of composition.

For the stability of the solution and also in the interest of simple storage it has proven advantageous if a quantity of {8-fluoro-2-[4-(3-methoxyphenyl)piperazine-1-yl]-3-[2-methoxy-5-(trifluoromethyl)phenyl]-3,4-dihydroquinazoline-4-yl}acetic acid is present in the above-mentioned ranges.

It is further preferred, within the scope of the invention, if the composition possesses a pH in the range of 7.5 to 8.5.

The aforementioned pH range has proved advantageous because it is a pH in the range of a physiological pH. It has furthermore been found that the solubility of the pharmaceutical composition according to the invention is again significantly better in the slightly alkaline range, i.e. in a range greater than 7.0, than at a pH value of 7.0 or less.

It is further preferred, within the scope of the invention, that the at least one excipient is present in the pharmaceutical composition in an amount of 1 to 5 equivalents, preferably of 2 to 5 equivalents and more preferably of 2.5 to 4.5 equivalents in relation to the content of {8-fluoro-2-[4-(3-methoxyphenyl)piperazine-1-yl]-3-[2-methoxy-5-(trifluoromethyl)phenyl]-3,4-dihydroquinazoline-4-yl}acetic acid.

It is further preferred within the scope of the invention, that said composition, in relation to the content of {8-fluoro-2-[4-(3-methoxyphenyl)piperazine-1-yl]-3-[2-methoxy-5-(trifluoromethyl)phenyl]-3,4-dihydroquinazoline-4-yl}acetic acid, possesses 1 to 10 equivalents, preferably 2 to 7 equivalents, and in particular 2.5 to 5 equivalents of cyclodextrin as well as 0 to 2.0 equivalents, preferably 0.5 to 1.5 equivalents, and in particular 0.75 to 0.9 equivalents of NaOH.

Within the framework of the invention the term "equivalents" is understood to mean "molar equivalents".

It has been found that adding less excipient than that given as the lower limit in the above-mentioned ranges causes inadequate stabilization of the solution. Adding amounts of excipient that exceed the aforementioned upper limits is not more advantageous in terms of the stability of the composition. It is furthermore feared that adding larger amounts of excipient will also lead to interactions with the active substance and thus tend to reduce the effectiveness of the composition.

Within the scope of the invention, particular preference is given to a pharmaceutical composition possessing the following constituents based on 100 ml of composition:
a) 0.25-2.0 g, preferably 0.5-1.25 g {8-fluoro-2-[4-(3-methoxyphenyl)piperazine-1-yl]-3-[2-methoxy-5-(trifluoromethyl)phenyl]-3,4-dihydroquinazoline-4-yl}acetic acid or a salt, a solvate or a solvate of a salt thereof,
b) 0.25-2.5 g, preferably 0.5 g-1.5 g of arginine,
c) 1.5-9.5 g, preferably 2.0-4.75 g of glucose,
d) 0.5-4.0 g, preferably 0.75-2.0 g of NaH2PO4, and
e) water,
wherein said composition has a pH in the range of 7.5 to 8.5, preferably 7.7 to 8.0.

Furthermore, within the scope of the invention, particular preference is given to a pharmaceutical composition possessing the following constituents based on 100 ml of composition:
a) 0.5-2.5 g, preferably 1.0-2.0 g {8-fluoro-2-[4-(3-methoxyphenyl)piperazine-1-yl]-3-[2-methoxy-5-(trifluoromethyl)phenyl]-3,4-dihydroquinazoline-4-yl}acetic acid or a salt, a solvate or a solvate of a salt thereof,
b) 10.0-30.0 g, preferably 12.5 g-22.5 g of HP-β-cyclodextrin, c) 0.0-350 mg, preferably 75-225 mg, in particular 100-125 mg of NaOH, and
d) water,
wherein said composition has a pH in the range of 7.5 to 8.5.

In the latter composition the NaOH is used preferably in the form of an approx. 0.1M aqueous solution.

It has been found that pharmaceutical compositions constituted in this way are particularly advantageous both as regards clinical effectiveness and also stability.

The pharmaceutical compositions according to the invention are generally produced by first producing an aqueous solution of the excipient and then adding {8-fluoro-2-[4-(3-methoxyphenyl)piperazine-1-yl]-3-[2-methoxy-5-(trifluoromethyl)phenyl]-3,4-dihydroquinazoline-4-yl}acetic acid to this solution, if necessary followed by the addition of other additives, such as the at least one sugar and/or the at least one buffer. After adding all the constituents, the pH of the pharmaceutical composition is adjusted to the desired value, with particular attention being paid to the fact that when the pH is adjusted from a value in the alkaline range towards the physiological pH value, by adding an acid or a buffer, this adjustment is carried out slowly and carefully to avoid any precipitation of {8-fluoro-2-[4-(3-methoxyphenyl)piperazine-1-yl]-3-[2-methoxy-5-(trifluoromethyl)phenyl]-3,4-dihydroquinazoline-4-yl}acetic acid resulting from an excessive local reduction in the pH value.

It is also possible to produce first of all individual solutions, with one solution containing the excipient and {8-fluoro-2-[4-(3-methoxyphenyl)piperazine-1-yl]-3-[2-methoxy-5-(trifluoromethyl)phenyl]-3,4-dihydroquinazoline-4-yl}acetic acid and the other solution containing the other excipients, such as for example the at least one sugar and/or the at least one buffer, where in the next step the solutions are adjusted to the desired pH and then mixed with each other.

It is further possible to dissolve, at least partially, the {8-fluoro-2-[4-(3-methoxyphenyl)piperazine-1-yl]-3-[2-methoxy-5-(trifluoromethyl)phenyl]-3,4-dihydroquinazoline-4-yl}acetic acid in an aqueous alkaline solution, e.g. a solution of an alkali metal hydroxide, preferably an NaOH solution, and then to add the excipient as well as, if necessary, the other constituents to the solution and, if necessary, to adjust the solution to the desired pH value.

It is further possible to lyophilize the solutions obtained by the above-mentioned methods in order to obtain the solid pharmaceutical compositions according to the invention.

The subject matter of the invention is thus also a method to produce a pharmaceutical composition according to the invention having the following steps:
A) Dissolving the at least one excipient in the water,
B) Adding {8-fluoro-2-[4-(3-methoxyphenyl)piperazine-1-yl]-3-[2-methoxy-5-(tri-fluoromethyl)phenyl]-3,4-dihydroquinazoline-4-yl}acetic acid or a salt, a solvate or a solvate of a salt thereof to the solution obtained in step A),
C) If necessary, add at least one sugar and/or at least one buffer,
D) Adjust the pH to the desired value in order to obtain a pharmaceutical composition, and
E) Sterile-filter the solution obtained in step D) and fill into suitable containers.
F) If necessary, perform a final sterilization of the solution obtained in step E) under heat.

The subject matter of the invention is also a method to produce a pharmaceutical composition according to the invention having the following steps:
I.) Dissolving the at least one excipient in a part of the water,
II.) Adding {8-fluoro-2-[4-(3-methoxyphenyl)piperazine-1-yl]-3-[2-methoxy-5-(tri-fluoromethyl)phenyl]-3,4-dihydroquinazoline-4-yl}acetic acid or a salt, a solvate or a solvate of a salt thereof to the solution obtained in step I.),
III.) If necessary, adjusting the pH of the solution obtained in step II.) to the desired value to obtain a first solution,
IV.) Dissolving at least one sugar and/or a buffer in a part of the water,
V.) If necessary, adjust the pH of the solution obtained in step IV.) to the desired value to obtain a second solution,
VI.) Mixing the first and second solution to obtain a pharmaceutical composition, and
VII.) Sterile filtration of the solution obtained in step VI.) and filling into suitable containers.
VIII.) If necessary, perform a final sterilization of the solution obtained in step VII.) under heat.

The subject matter of the invention is also a method to produce a pharmaceutical composition according to the invention having the following steps:
a.) Adding {8-fluoro-2-[4-(3-methoxyphenyl)piperazine-1-yl]-3-[2-methoxy-5-(tri-fluoromethyl)phenyl]-3,4-dihydroquinazoline-4-yl}acetic acid or a salt, a solvate or a solvate of a salt to an aqueous NaOH solution, preferably an aqueous 0.1M NaOH solution to produce a solution or suspension,
b.) Adding water to the solution or suspension obtained in step a.),
c.) Adding cyclodextrin and NaCl to the solution or suspension obtained in step b.),
d.) Sterile filtration of the solution obtained in step c.) and fill into suitable containers.
e.) If necessary, perform a final sterilization of the solution obtained in step d.) under heat.

The subject matter of the invention is in addition a method to produce a solid pharmaceutical composition, wherein a pharmaceutical composition produced according to the aforementioned methods is lyophilized.

The {8-fluoro-2-[4-(3-methoxyphenyl)piperazine-1-yl]-3-[2-methoxy-5-(trifluoromethyl)phenyl]-3,4-dihydroquinazoline-4-yl}acetic acid, or salts, solvates and solvates of the salts thereof, which are used to produce the pharmaceutical compositions according to the invention, are known and can be produced, for example, by the method described in WO 2006/133822.

The production takes place in particular by the saponification of the ester of a compound having the formula (II)

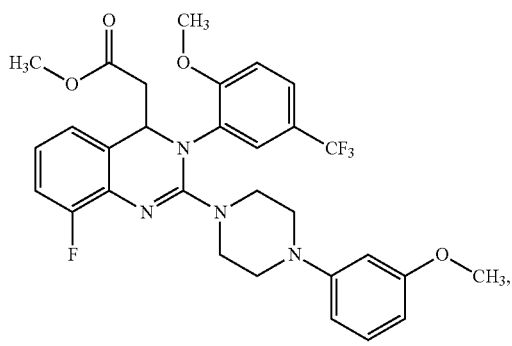

(II)

with a base.

The compound having the formula (II) can be produced by reacting a compound having the formula (III)

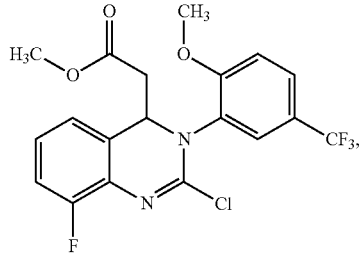

(III)

with a compound having the formula (IV) in the presence of a base.

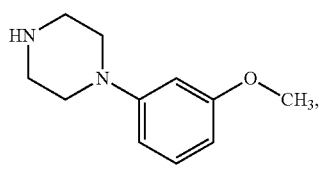

The compound having the formula (III) can be produced by reacting a compound having the formula (V)

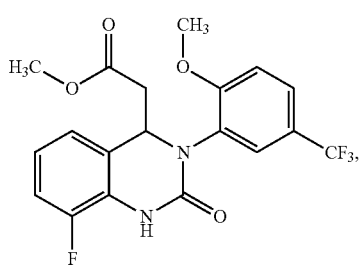

with phosphorus oxychloride, phosphorus trichloride or phosphorus pentachloride in the presence of a base.

The compound having the formula (V) can be produced by reacting a compound having the formula (VI)

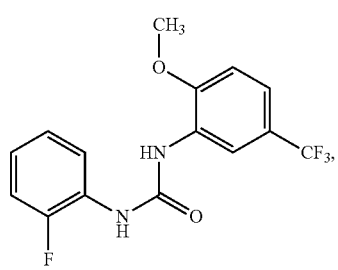

in the first step with acrylic acid methyl ester in the presence of a palladium catalyst and oleum, and in the second step with a base.

Compounds having the formulae (IV) and (VI) are in principle known to a person skilled in the art or can be produced by customary methods known from the literature.

The saponification of the ester of a compound having the formula (II) to form {8-fluoro-2-[4-(3-methoxyphenyl)piperazine-1-yl]-3-[2-methoxy-5-(trifluoromethyl)phenyl]-3,4-dihydroquinazoline-4-yl}acetic acid is achieved by reacting a compound having the formula (II) with a base in an inert solvent, in a temperature range from 18° C. up to reflux of the solvent, preferably at 18 to 50° C., more preferably at 20 to 30° C., at normal pressure, within a period of, for example, 0.5 to 10 hours, preferably within 1 to 5 hours.

Bases are, for example, alkali hydroxides, such as sodium, lithium or potassium hydroxide, or alkali carbonates, such as cesium carbonate, sodium or potassium carbonate, or alcoholates such as sodium or potassium methanolate, or sodium or potassium ethanolate, where the base may be present in aqueous solution.

Inert solvents are, for example, ethers, such as 1,2-dimethoxyethane, methyl tert-butyl ether (MTBE), dioxane, tetrahydrofuran, glycol dimethyl ether or diethylene glycol dimethyl ether, alcohols such as methanol, ethanol, n-propanol, iso-propanol, n-butanol or tert-butanol, or water, or mixtures of solvents.

Sodium hydroxide in water and MTBE are preferred.

The synthesis of a compound having the formula (II) from a compound having the formula (III) and a compound having the formula (IV), in the presence of a base, takes place in an inert solvent, in a temperature range from 40° C. up to reflux of the solvent, preferably at reflux of the solvent, at normal pressure, within for example 2 to 48 hours, preferably within 4 to 12 hours.

Bases are, for example, amine bases such as 1,8-diazabicyclo[5.4.0]undec-7-ene (DBU), 1-(3-methoxyphenyl)piperazine or triethylamine, or other bases such as potassium tert-butylate.

Inert solvents are, for example, chlorobenzene or ethers such as 1,2 dimethoxyethane, dioxane, glycol dimethyl ether or diethylene glycol dimethyl ether.

DBU in dioxane is preferred.

The conversion of a compound having the formula (V) to a compound having the formula (III) takes place by reacting a compound having the formula (V) with phosphorus oxychloride, phosphorus trichloride or phosphorus pentachloride, with phosphorus oxychloride being preferred, in the presence of a base in an inert solvent, in a temperature range from 40° C. up to reflux of the solvent, preferably at reflux of the solvent, at normal pressure, within for example 1 to 48 hours, preferably within 2 to 12 hours.

Bases are, for example, amines such as 1,8-diazabicyclo[5.4.0]undec-7-ene (DBU), pyridine or triethylamine, or other bases such as potassium tert-butylate.

Inert solvents are for example hydrocarbons such as benzene, xylene, toluene or chlorobenzene.

DBU in chlorobenzene is preferred.

The conversion of a compound having the formula (VI) to a compound having the formula (V) takes place, in the first step, by reacting a compound of the formula (VI) with acrylic acid methyl ester in the presence of a palladium catalyst and oleum in a solvent, in a temperature range from 0° C. to 40° C., preferably at room temperature, and in the second step by reaction with a base in an inert solvent, in a temperature range from 40° C. up to reflux of the solvent, preferably at reflux of the solvent, at normal pressure, within for example 1 to 48 hours, preferably within 2 to 12 hours.

Palladium catalysts in the first step are, for example, palladium(II) acetate, bis(triphenylphosphine)palladium(II) chloride, tetrakis(triphenylphosphine)palladium(0), bis(tri(o-tolyl)phosphine)palladium-(II)-chloride, or a palladium catalyst produced from bis(acetonitrile)dichloropalladium or palladium(II) acetate and a ligand, for example tris(o-tolyl)phosphine, triphenylphosphine or diphenylphosphino ferrocene.

Solvents in the first step are, for example, organic acids such as acetic acid or propionic acid.

Palladium(II) acetate in acetic acid is preferred.

Bases in the second step are, for example, DBU, triethylamine or diisopropylethylamine.

Inert solvents in the second step are, for example, ethers such as 1,2-dimethoxyethane, dioxane, glycol dimethyl ether or diethylene glycol dimethyl ether, hydrocarbons such as benzene, xylene or toluene, or other solvents such as isobutyronitrile, acetonitrile, acetone, nitrobenzene, dimethylformamide, dimethylacetamide, dimethylsulfoxide or N-methylpyrrolidone.

DBU in acetone is preferred.

The production of the {8-fluoro-2-[4-(3-methoxyphenyl)piperazine-1-yl]-3-[2-methoxy-5-(trifluoromethyl)phenyl]-3,4-dihydroquinazoline-4-yl}acetic acid used to produce the pharmaceutical composition according to the invention is described in more detail, by way of example, in the following Synthesis Diagram 1. This synthesis diagram is nothing more than an example and should in no way be understood as restrictive.

Synthesis Diagram 1

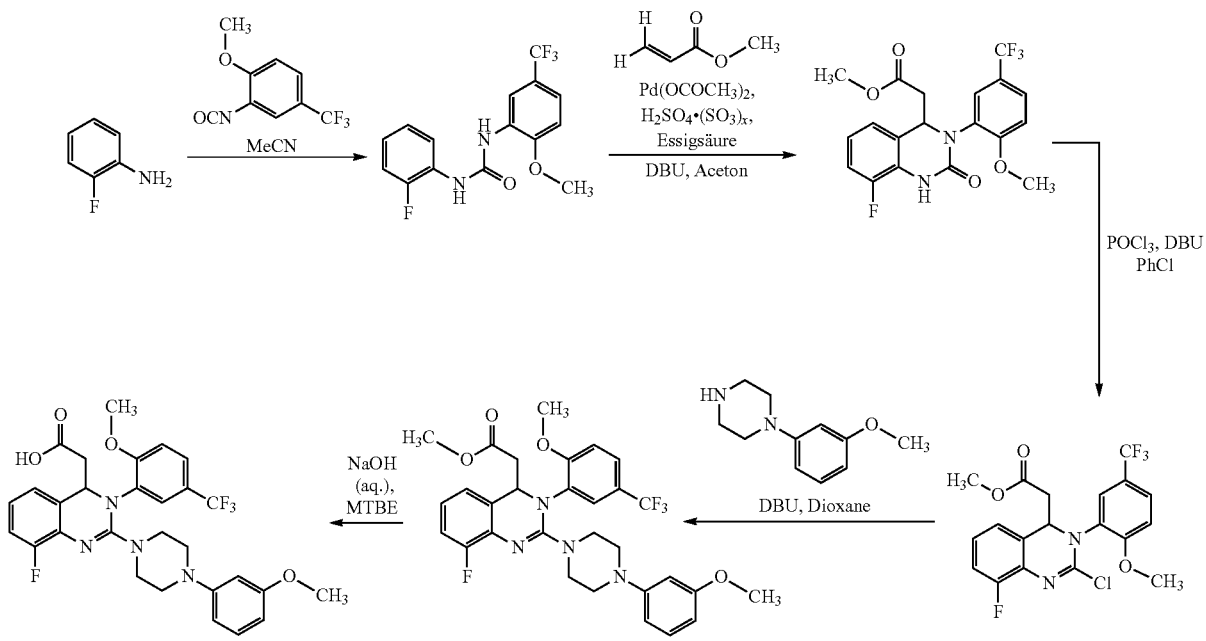

[[Translation key:
Essigsäure = acetic acid]

As already mentioned further above, the {8-fluoro-2-[4-(3-methoxyphenyl)piperazine-1-yl]-3-[2-methoxy-5-(trifluoromethyl)phenyl]-3,4-dihydroquinazoline-4-yl}acetic acid is used preferably in the form of the S-enantiomer. This S-enantiomer can be produced as shown, for example, in the following Synthesis Diagram 2.

Synthesis Diagram 2

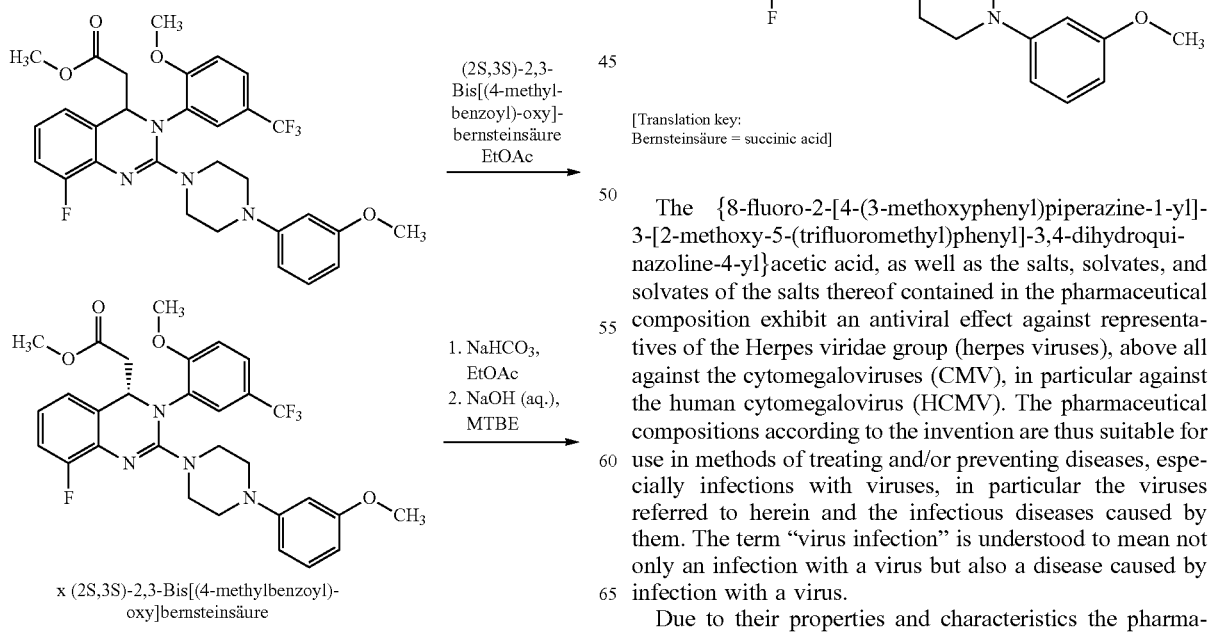

[Translation key:
Bernsteinsäure = succinic acid]

The {8-fluoro-2-[4-(3-methoxyphenyl)piperazine-1-yl]-3-[2-methoxy-5-(trifluoromethyl)phenyl]-3,4-dihydroquinazoline-4-yl}acetic acid, as well as the salts, solvates, and solvates of the salts thereof contained in the pharmaceutical composition exhibit an antiviral effect against representatives of the Herpes viridae group (herpes viruses), above all against the cytomegaloviruses (CMV), in particular against the human cytomegalovirus (HCMV). The pharmaceutical compositions according to the invention are thus suitable for use in methods of treating and/or preventing diseases, especially infections with viruses, in particular the viruses referred to herein and the infectious diseases caused by them. The term "virus infection" is understood to mean not only an infection with a virus but also a disease caused by infection with a virus.

Due to their properties and characteristics the pharmaceutical compositions according to the invention can be used to produce drugs that are suitable for use in methods of preventing and/or treating diseases, in particular virus infections.

The following areas of indication can be mentioned, by way of example:
1) Treatment and prevention of HCMV infections in AIDS patients (retinitis, pneumonitis, gastrointestinal infections).
2) Treatment and prevention of cytomegalovirus infections in bone marrow and organ transplant patients who often contract life-threatening HCMV pneumonitis or encephalitis, as well as gastrointestinal and systemic HCMV infections.
3) Treatment and prevention of HCMV infections in neonates and infants.
4) Treatment of acute HCMV infection in pregnant women.
5) Treatment of HCMV infection in immune-suppressed patients suffering from cancer and undergoing cancer therapy.
6) Treatment of HCMV-positive cancer patients with the aim of reducing HCMV-mediated tumour progression (cf. J. Cinatl, et al., *FEMS Microbiology Reviews* 2004, 28, 59-77).

The pharmaceutical compositions according to the invention are preferably used to produce drugs which are suitable for use in methods of preventing and/or treating infections with a representative of the Herpes viridae group, in particular a cytomegalovirus, in particular the human cytomegalovirus.

Due to their pharmacological properties and characteristics, the pharmaceutical compositions according to the invention can be used by themselves and, if needed, also in combination with other active substances, especially antiviral substances such as for example valganciclovir, ganciclovir, valacyclovir, acyclovir, foscarnet, cidofovir and related derivatives in methods of treating and/or preventing virus infections, in particular HCMV infections.

Further subject matter of the present invention is the use of the pharmaceutical compositions according to the invention in a method of treating and/or preventing diseases, preferably virus infections, in particular infections with the human cytomegalovirus (HCMV) or another representative of the Herpes viridae group.

Further subject matter of the present invention is the use of the pharmaceutical compositions according to the invention in a method of treating and/or preventing diseases, in particular the aforementioned diseases.

Further subject matter of the present invention is the use of the pharmaceutical compositions according to the invention to produce a drug for use in methods of treating and/or preventing diseases, in particular the aforementioned diseases.

Further subject matter of the present invention is a method of treating and/or preventing diseases, in particular the aforementioned diseases, using an antivirally effective amount of the pharmaceutical compositions according to the invention.

The term "antivirally effective amount" denotes the pharmaceutical compositions according to the invention in a dose of at least 0.001 mg/kg.

In general, it has proved to be advantageous to administer the pharmaceutical compositions in such a way that about 0.001 to 10 mg per kg, preferably 0.01 to 5 mg per kg body weight of {8-fluoro-2-[4-(3-methoxyphenyl)piperazine-1-yl]-3-[2-methoxy-5-(trifluoromethyl)phenyl]-3,4-dihydroquinazoline-4-yl}acetic acid is administered.

Nevertheless, it may be necessary to deviate from the stated amounts, namely depending on body weight, individual response to the active substance and the time and interval at which it is applied. For example, in certain cases it may be sufficient to get by with less than the aforementioned minimum amount, while in other cases the stated upper limit has to be exceeded. When administering large amounts it may be recommendable to distribute these in several individual doses over the course of a day.

The invention will now be described in detail on the basis of non-restrictive examples.

Unless otherwise stated, the percentages given in the following tests and examples are weight percentages, parts are weight proportions, solvent ratios, dilution ratios and concentrations of liquid solutions relate, in each case, to the volume.

LIST OF ABBREVIATIONS

ACN Acetonitrile

API-ES-pos. Atmospheric pressure ionization, electrospray, positive (in MS)

API-ES-neg. Atmospheric pressure ionization, electrospray, negative (in MS)

ca. circa

CI, $NH_3$ chemical ionization (with ammonia)

DBU 1,8-Diazabicyclo[5.4.0]undec-7-ene

DMAP 4-(Dimethylamino)pyridine

DMSO Dimethyl sulfoxide

ESTD external standardization h hour(s)

HPLC high pressure liquid chromatography conc. concentrated min. minutes

MS mass spectroscopy

MTBE Methyl tert-butylether

NMR nuclear magnetic resonance spectroscopy $R_T$ retention time (in HPLC)

VTS vacuum drying cabinet

General HPLC Methods:

Method 1 (HPLC): Instrument: HP 1050 with variable wavelength detection; column: Phenomenex Prodigy ODS (3) 100A, 150 mm×3 mm, 3 μm; Eluent A: (1.0 g $KH_2PO_4$+ 1.0 mL $H_3PO_4$)/1 water, Eluent B: acetonitrile; gradient: 0 min 10% B, 25 min 80% B, 35 min 80% B; flow: 0.5 ml/min; temp.: 45° C.; UV detection: 210 nm.

Method 2 (HPLC): Instrument: HP 1050 with variable wavelength detection; column: Chiral AD-H, 250 mm×4.6 mm, 5 μm; Eluent A: n-heptane+0.2% diethylamine, Eluent B: isopropanol+0.2% diethylamine; gradient: 0 min 12.5% B, 30 min 12.5% B; flow: 1 ml/min; temp.: 25° C.; UV detection: 250 nm.

Method 3 (HPLC): Instrument: HP 1050 with variable wavelength detection; column: Chiral AD-H, 250 mm×4.6 mm, 5 μm; Eluent A: n-heptane+0.2% diethylamine, Eluent B: isopropanol+0.2% diethylamine; gradient: 0 min 25% B, 15 min 25% B; flow: 1 ml/min; temp.: 30° C.; UV detection: 250 nm.

EXAMPLES

A) Production of {8-fluoro-2-[4-(3-methoxyphenyl)piperazin-1-yl]-3-[2-methoxy-5-(trifluoromethyl)phenyl]-3,4-dihydroquinazoline-4-yl}acetic acid

Example 1A

N-(2-fluorophenyl)-N'-[2-methoxy-5-(trifluoromethyl)phenyl]urea

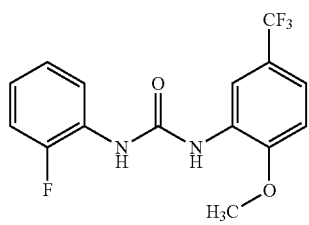 [SMILES: COc1ccc(C(F)(F)F)cc1NC(=O)Nc1ccccc1F]

2-methoxy-5-trifluoromethylphenyl isocyanate (78 kg) is melted at approx. 35° C. and dissolved in acetonitrile (a total of approx. 270 l), then 2-fluoroaniline (39.9 kg) is added and rinsed with acetonitrile (approx. 25 l). The resulting clear solution is agitated for 4 h at reflux and then cooled to approx. 75° C. Once this temperature is reached, the solution is inoculated with seed crystals of the desired end product (200 g), agitated for an additional 15 min., and then cooled to 0° C. over the course of 3 h. The resulting crystalline product is isolated by centrifugation, washed with cold acetonitrile (twice using approx. 13 l), and dried at 45° C. in the VTS under purging with nitrogen (approx. 3.5 h). A total of 101.5 kg of N-(2-fluorophenyl)-N'-[2-methoxy-5-(trifluormethyl)phenyl]urea is thus obtained as a solid, corresponding to 85.9% of theory.

$^1$H NMR (300 MHz, $d_6$-DMSO): δ=8.93 (s, 1H), 8.84 (s, 1H), 8.52 (d, $^3$J=2.3, 2H), 7.55 (d, $^2$J=7.7, 1H), 7.38-7.26 (m, 3H), 7.22 (d, $^2$J=8.5, 1H), 4.00 (s, 3H) ppm;

MS (API-ES-pos.): m/z=409 [(M+H)$^+$, 100%];

HPLC (Method 1): $R_T$=22.4 and 30.6 min.

Example 2A

Methyl-(2Z)-3-[3-fluoro-2-({[2-methoxy-5-(trifluoromethyl)phenyl]carbamoyl}amino)-phenyl]acrylate

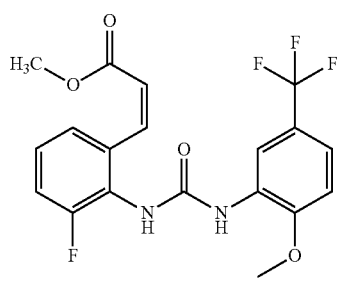 [SMILES: COC(=O)/C=C\c1cccc(F)c1NC(=O)Nc1cc(C(F)(F)F)ccc1OC]

N-(2-fluorophenyl)-N'-[2-methoxy-5-(trifluoromethyl)phenyl]urea (51 kg) is dissolved in acetic acid (approx. 430 l) in one reactor in a nitrogen atmosphere. Methyl acrylate (20.1 kg) is added to the resulting solution and the resulting suspension is agitated until further use. Acetic acid (950 l) is placed in a second reactor, oleum (57 kg) is carefully added and palladium (II) acetate (7 kg) is dissolved in the mixture. The suspension formed in the first reactor is then added to the mixture contained in the second reactor over the course of approx. 2 h; the reaction mixture is overflowed with a mixture of 96% nitrogen and 4% oxygen and the resulting reaction mixture is agitated for approx. 18 h at room temperature. Part of the acetic acid (approx. 900 l) is then distilled off; water (approx. 500 l) is added to the remaining reaction mixture over the course of approx. 1 h and the resulting suspension is agitated for 1 h. The resulting particulate matter is filtered off, washed once with a mixture of acetic acid and water (1:1) and twice with water, and finally dried at approx. 30 mbar and 50° C. A total of 44.8 kg of methyl-(2Z)-3-[3-fluoro-2-({[2-methoxy-5-(trifluoromethyl)phenyl]carbamoyl}amino)phenyl]acrylate is thus obtained as a solid, corresponding to 65.0% of theory.

$^1$H NMR (300 MHz, $d_6$-DMSO): δ=9.16 (s, 1H), 8.84 (s, 1H), 8.45 (d, 1.7 Hz, 1H), 7.73 (m, 2H), 7.33 (m, 3H), 7.22 (d, 8.6 Hz, 1H), 6.70 (d, 16 Hz, 1H), 3.99 (s, 3H), 3.71 (s, 3H) ppm;

MS (API-ES-pos.): m/z=429.9 [(M+NH$_4$)$^+$]; 412.9 [(M+H)$^+$]

HPLC: $R_T$=46.4 min.

Instrument: HP 1100 with variable wavelength detection; column: Phenomenex Prodigy ODS (3) 100A, 150 mm×3 mm, 3 μm; Eluent A: (1.36 g KH$_2$PO$_4$+0.7 ml H$_3$PO$_4$)/1 of water, Eluent B: acetonitrile; gradient: 0 min 20% B, 40 min 45% B, 50 min 80% B, 65 min 80% B; flow: 0.5 ml/min; temp.: 55° C.; UV detection: 210 nm.

Example 3A

{8-fluoro-3-[2-methoxy-5-(trifluoromethyl)phenyl]-2-oxo-1,2,3,4-tetrahydroquinazoline-4-yl}methyl acetate

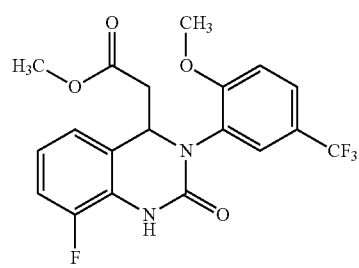 [SMILES: COC(=O)CC1c2cccc(F)c2NC(=O)N1c1cc(C(F)(F)F)ccc1OC]

The compound in Example 2A (75 kg) is suspended in acetone (1600 l), and DBU (5.7 kg) is added. The resulting suspension is heated to reflux and agitated for 4 h at reflux. The resulting solution is cooled to a jacket temperature of 55° C. and filtered through kieselguhr. Part of the solvent (approx. 1125 l) is removed by distillation and the remaining residue is cooled for 2 h to 0° C. The resulting solid is separated out by centrifugation, washed twice using cold acetone (approx. 15 l), and dried overnight at 45° C. under reduced pressure and purging with nitrogen to constant mass. A total of 58.3 kg of {8-fluoro-3-[2-methoxy-5-(trifluoromethyl)phenyl]-2-oxo-1,2,3,4-tetrahydroquinazoline-4-yl}methyl acetate is thus obtained as a solid, corresponding to 84.1% of theory. HPLC (Method 1): $R_T$=19.4 min.

Example 4A (2S,3S)-2,3-bis[(4-methylbenzoyl)oxy]succinic acid-{(4S)-8-fluoro-2-[4-(3-methoxyphenyl) piperazine-1-yl]-3-[2-methoxy-5-(trifluoromethyl)phenyl]-3,4-dihydroquinazoline-4-yl}methyl acetate (1:1 salt) chlorination/amination/crystallization

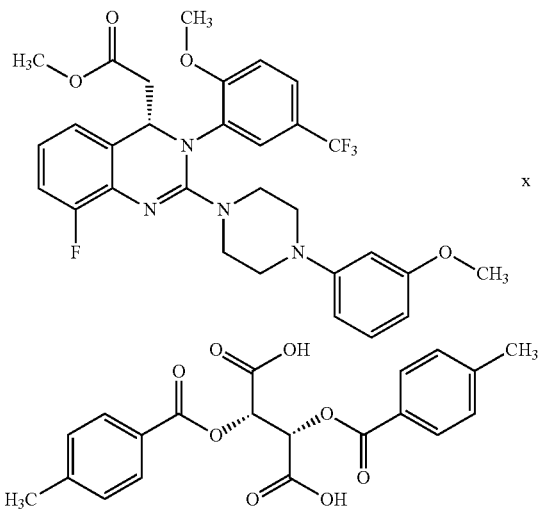

A solution of {8-fluoro-3-[2-methoxy-5-(trifluoromethyl)phenyl]-2-oxo-1,2,3,4-tetrahydroquinazoline-4-yl}methyl acetate (Example 3A, 129.2 kg) in chlorobenzene (800 l) is heated to reflux and azeotropically dried. Phosphorous oxychloride (144 kg) is added, and the reaction mixture is agitated for 3 h at reflux. Next, DBU (95 kg) and chlorobenzene (45 l) are added and agitated for an additional 9 h at reflux. The reaction mixture is cooled to room temperature, hydrolyzed by adding water, diluted with chlorobenzene (80 l), and neutralized with an aqueous solution of ammonia (25%). The phases are separated, the organic phase is washed with water and the solvent is distilled off. The remaining residue is dissolved in dioxane (170 l). 3-methoxyphenylpiperazine (66 kg), DBU (52 kg), and an additional 90 l of dioxane are added and the reaction mixture is heated for 4 h at reflux. The reaction mixture is cooled to room temperature, added to ethyl acetate (1300 l), washed once with water, 3 times with 0.2 N HCl, and once with an aqueous solution of NaCl, and the solvent is distilled off. The resulting residue is dissolved in ethyl acetate (800 l) and added to a solution of (2S,3S)-2,3-bis[(4-methylbenzoyl)oxy]-succinic acid (121 kg) in ethyl acetate (600 l). The resulting mixture is agitated for approx. 60 min. at room temperature and then inoculated with (2S,3S)-2,3-bis[(4-methylbenzoyl)oxy]-succinic acid-{(4S)-8-fluoro-2-[4-(3-methoxyphenyl)piperazine-1-yl]-3-[2-methoxy-5-(trifluoromethyl)-phenyl]-3,4-dihydroquinazoline-4-yl}methyl acetate and agitated for 3 days at room temperature. It is then cooled to 0-5° C. and agitated for an additional 3 h. The suspension is filtered and the remaining solid is rewashed in batches with ethyl acetate. A total of about 141 kg (calculated as dry weight) of the salt is thus obtained as a solid, corresponding to around 46.2% of theory, in three stages (chlorination, amination, and crystallization) compared to the racemate.

$^1$H NMR (300 MHz, $d_6$-DMSO): δ=7.90 (d, $^2$J=7.8, 4H), 7.56 (d, $^2$J=8.3, 1H), 7.40 (d, $^2$J=7.8, 4H), 7.28-7.05 (m, 4H), 6.91-6.86 (m, 2H), 6.45 (d, $^2$J=8.3, 1H), 6.39-6.36 (m, 2H), 5.82 (s, 2H), 4.94 (m, 1H), 4.03 (q, $^2$J=7.1, 2H), 3.83 (brs, 3H), 3.69 (s, 3H), 3.64 (s, 3H), 3.47-3.36 (m, 8H and water, 2H), 2.98-2.81 (m, 5H), 2.58-2.52 (m, 1H), 2.41 (s, 6H), 1.99 (s, 3H), 1.18 (t, $^2$J=7.2, 3H) ppm; HPLC (Method 1): $R_T$=16.6 and 18.5 min.

Example 5A (2S,3S)-2,3-bis[(4-methylbenzoyl)oxy]succinic acid-{(4S)-8-fluoro-2-[4-(3-methoxyphenyl)piperazine-1-yl]-3-[2-methoxy-5-(trifluoromethyl)phenyl]-3,4-dihydroquinazoline-4-yl}methyl acetate (1:1 salt)/Recrystallization (2S,3S)-2,3-bis[(4-methylbenzoyl)oxy]-succinic acid-(S){(4S)-8-fluoro-2-[4-(3-methoxyphenyl)piperazine-1-yl]-3-[2-methoxy-5-(trifluoromethyl)phenyl]-3,4-dihydroquinazoline-4-yl}acetic acid methyl ester (1:1 salt) (141 kg, calculated as dry weight) is suspended in ethyl acetate (1400 l) and dissolved by heating to reflux (77° C.). The solution is filtered and slowly cooled to room temperature, which results in spontaneous crystallization. The suspension is agitated for 16 h at RT, and then cooled to 0-5° C. and agitated for an additional 3 h. The suspension is filtered and the remaining solid is rewashed with cold ethyl acetate. The crystals are dried for 16 h in a vacuum at around 40° C. A total of 131.2 kg of the salt is obtained as a solid, corresponding to 93.0% of theory.

HPLC (Method 1): $R_T$=16.9 and 18.8 min.;
HPLC (Method 3): 99.9% e.e.

Example 6A (S)-{8-fluoro-2-[4-(3-methoxyphenyl)piperazine-1-yl]-3-(2-methoxy-5-trifluoromethylphenyl)-3,4-dihydroquinazoline-4-yl}acetic acid

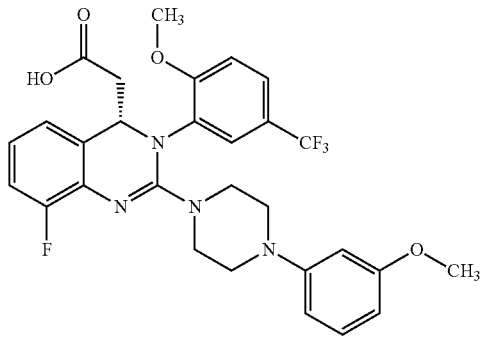 [SMILES: COc1cccc(N2CCN(C3=Nc4c(F)cccc4[C@H](CC(=O)O)N3c3cc(C(F)(F)F)ccc3OC)CC2)c1]

A mixture of (2S,3S)-2,3-bis[(4-methylbenzoyl)oxy]succinic acid-{(4S)-8-fluoro-2-[4-(3-methoxyphenyl)piperazine-1-yl]-3-[2-methoxy-5-(trifluoromethyl)phenyl]-3,4-dihydroquinazoline-4-yl}acetic acid methyl ester (1:1 salt) (30.8 kg), sodium bicarbonate (16.4 kg), and water (315 l) is mixed with MTBE (160 l). The phases are separated and the organic phase is treated with 35 l of an approximately seven-percent aqueous solution of sodium bicarbonate. The phases are separated and the organic phase is added to 125 l of an approximately four-percent aqueous solution of sodium hydroxide. The reaction mixture is heated to reflux, the solution is evaporated to dryness, and the reactor contents are then agitated for an additional 5 h at 55-60° C. The reaction mixture is then added at approx. 22° C. to MTBE (160 l) and water (65 l) and agitated. The phases are separated and the organic phase is extracted with an approximately six-percent aqueous solution of sodium chloride (30 l). The combined aqueous phases are mixed with water (25 l) and MTBE (160 l) and the pH value is adjusted to approx. 6.5 with approx. 1 N of hydrochloric acid. The organic phase is separated out, the solvent is evaporated to dryness, and the residue is dissolved in acetone (approx. 75 l). The solvent is changed to acetone (6 distillations with approx. 130 l each). The final product is then precipitated by adding water, isolated through centrifugation, and dried in a vacuum dryer. A total of 16.5 kg of (S)-[8-fluoro-2-[4-(3-methoxyphenyl) piperazine-1-yl]-3-(2-methoxy-5-trifluoromethylphenyl)-3,4-dihydroquinazoline-4-yl]acetic acid is thus obtained as an amorphous solid, corresponding to 96.4% of theory.

$^1$H NMR (300 MHz, d$_6$-DMSO): δ=7.53 (d, $^2$J=8.4, 1H), 7.41 (brs, 1H), 7.22 (d, $^2$J=8.5, 1H), 7.09-7.01 (m, 2H), 6.86 (m, 2H), 6.45 (dd, $^2$J=8.2, $^3$J=1.8, 1H), 6.39-6.34 (m, 2H), 4.87 (t, $^2$J=7.3, 1H), 3.79 (brs, 3H), 3.68 (s, 3H), 3.50-3.38 (m, 4H), 2.96-2.75 (m, 5H), 2.45-2.40 (m, 1H) ppm;

MS (API-ES-neg.): m/z=571 [(M+H), 100%];

HPLC (Method 1): R$_T$=15.1 min;

HPLC (Method 2): 99.8% e.e.; Pd (ICP): <1 ppm.

B) Exemplary Embodiments of Pharmaceutical Compositions According to the Invention Example 1

Production of a Pharmaceutical Composition Using Cyclodextrin

In a three-necked flask, 30.03 g of hydroxypropyl-β-cyclodextrin HP5 (Kleptose HPB, Roquette) are mixed with 68.365 g of water for injection purposes, and 6.6 g of a 1 M solution of sodium hydroxide is added to the mixture. Following the addition of 5.005 g of the compound from Example 6A, the mixture is heated to 50° C. and agitated for 24 h until a clear solution is formed. The solution is sterile filtered (pore diameter 0.22 μm) and transferred under aseptic conditions to sterile 20-ml glass containers. The filled glass containers are sealed with infusion plugs and flange caps.

Example 2

Production of a First Pharmaceutical Composition Using Arginine as an Excipient

To produce a first stock solution, 262.38 mg of L-arginine are weighed in a 25-ml volumetric flask and then dissolved in approx. 22 ml of water for injection. 504.51 mg of the compound from Example 6A are added to the resulting arginine solution, and the mixture is agitated for approx. 1 h until a clear solution is obtained. The volume is then topped up with water for injection purposes.

To produce a second stock solution, 40.05 mg of sodium dihydrogen phosphate dihydrate are weighed in a 50 ml volumetric flask and dissolved in approx. 48 ml of water for injection. The mixture is agitated until a clear solution is obtained and the volume is topped up with water for injection.

To produce a solution with a concentration of 10 mg/ml of {8-fluoro-2-[4-(3-methoxyphenyl)piperazine-1-yl]-3-[2-methoxy-5-(trifluoromethyl)phenyl]-3,4-dihydroquinazoline-4-yl}acetic acid, 12.5 ml of the first stock solution are mixed with 10 ml of the second stock solution in a 25-ml volumetric flask and the pH is slowly and carefully adjusted with approx. 200 μl of 1 M HCl. The volume is then topped up with the second stock solution in order to obtain a mixture with a final pH of 7.9.

Using this protocol, compositions with varying concentrations of {8-fluoro-2-[4-(3-methoxyphenyl)piperazine-1-yl]-3-[2-methoxy-5-(trifluoromethyl)phenyl]-3,4-dihydroquinazoline-4-yl}acetic acid can be produced and only the quantity of the first stock solution used must be varied. However, it is important that the pH does not vary too much and particularly that it shifts not towards the acid range.

The solutions thus obtained are sterile filtered (pore diameter 0.22 μm) and transferred under aseptic conditions to sterile containers. The containers are sealed with infusion plugs and flange caps.

Example 3

Production of a Second Pharmaceutical Composition Using Arginine as an Excipient To produce a first stock solution, 2.1 g of L-arginine are dissolved in 88.8 g of water for injection purposes. 2 g of the compound from Example 6A are added to the resulting arginine solution, and the mixture is agitated for approx. 1 h until a clear solution is obtained. The pH value of the resulting solution is adjusted to 7.8 by adding 1 M HCl dropwise; it is important that the HCl be added slowly so that the compound from Example 6A does not precipitate. If necessary, the volume of solution is then topped up to 100 ml.

To produce a second stock solution, 3.1 g of sodium dihydrogen phosphate dihydrate and 8.4 g of glucose are weighed in an appropriate container and dissolved in approx. 74.5 g of water for injection. The mixture is agitated until a clear solution is obtained, and the pH of the resulting solution is adjusted to 7.8 using 1 M NaOH. Finally, if necessary, the volume of solution is topped up to 100 ml.

To produce a solution with a concentration of 10 mg/ml of {8-fluoro-2-[4-(3-methoxyphenyl)piperazine-1-yl]-3-[2-methoxy-5-(trifluoromethyl)phenyl]-3,4-dihydroquinazoline-4-yl}acetic acid, 50.5 g of the first stock solution are mixed with 53.0 g of the second stock solution and agitated for 5 min.

Using this protocol, compositions with varying concentrations of {8-fluoro-2-[4-(3-methoxyphenyl)piperazine-1-yl]-3-[2-methoxy-5-(trifluoromethyl)phenyl]-3,4-dihydroquinazoline-4-yl}acetic acid can be produced and only the quantity of the first stock solution used must be varied.

The solutions thus obtained are sterile filtered (pore diameter 0.22 μm) and transferred under aseptic conditions to sterile containers. The containers are sealed with infusion plugs and flange caps.

Example 4

Production of a Third Pharmaceutical Composition Using Arginine as an Excipient

To produce a first stock solution, 1.05 g of L-arginine and 1 g of the compound from Example 6A are dissolved in approx. 50.0 g of water for injection purposes in a 100-ml volumetric flask and the mixture is agitated until a clear solution is obtained. The pH value of the resulting solution is adjusted to 7.8 by adding 0.1 M HCl dropwise (approx. 43.5 ml); it is important that the HCl be added slowly so that the compound from Example 6A does not precipitate. Finally, the volume of solution is topped up to 100 ml.

To produce a second stock solution, 1.56 g of sodium dihydrogen phosphate dihydrate and 4.18 g of glucose are dissolved in approx. 80.0 g of water for injection purposes in a 100-ml volumetric flask. The mixture is agitated until a clear solution is obtained, and the pH of the resulting solution is adjusted to 7.8 using 1 M NaOH (approx. 9.1 ml). Finally, the volume of solution is topped up to 100 ml.

To produce a solution with a concentration of 5 mg/ml of {8-fluoro-2-[4-(3-methoxyphenyl)piperazine-1-yl]-3-[2-methoxy-5-(trifluoromethyl)phenyl]-3,4-dihydroquinazoline-4-yl}acetic acid, 50.24 g of the first stock solution are mixed with 51.35 g of the second stock solution and agitated for 5 min.

Using this protocol, compositions with varying concentrations of {8-fluoro-2-[4-(3-methoxyphenyl)piperazine-1-yl]-3-[2-methoxy-5-(trifluoromethyl)phenyl]-3,4-dihydroquinazoline-4-yl}acetic acid can be produced and only the quantity of the first stock solution used must be varied.

The solutions thus obtained are sterile filtered (pore diameter 0.22 μm) and transferred under aseptic conditions to sterile containers. The containers are sealed with infusion plugs and flange caps.

Example 5

Production of a Fourth Pharmaceutical Composition Using Arginine as an Excipient To produce a first stock solution, 2.11 g of L-arginine are mixed with 2.01 g of the compound from Example 6A in a 100-ml volumetric flask and the volume is topped up with water for injection. The pH value of this first stock solution was 9.8.

To produce a second stock solution, 3.12 g of sodium dihydrogen phosphate dihydrate, 8.35 g of glucose, and 0.50 g of NaCl are dissolved in approx. 80.0 g of water for injection in a 100-ml volumetric flask. The mixture is agitated until a clear solution is obtained, and the pH of the resulting solution is adjusted to 6.5 using 1 M NaOH (approx. 9.7 ml). Finally, the volume of solution is topped up to 100 ml.

To produce a solution with a concentration of 10 mg/ml of {8-fluoro-2-[4-(3-methoxyphenyl)piperazine-1-yl]-3-[2-methoxy-5-(trifluoromethyl)phenyl]-3,4-dihydroquinazoline-4-yl}acetic acid, 50.50 g of the first stock solution are mixed with 52.65 g of the second stock solution and agitated for 5 min.

Using this protocol, compositions with varying concentrations of {8-fluoro-2-[4-(3-methoxyphenyl)piperazine-1-yl]-3-[2-methoxy-5-(trifluoromethyl)phenyl]-3,4-dihydroquinazoline-4-yl}acetic acid can be produced and only the quantity of the first stock solution used must be varied or the pH may need to be adjusted.

The solutions thus obtained are sterile filtered (pore diameter 0.22 μm) and transferred under aseptic conditions to sterile containers. The containers are sealed with infusion plugs and flange caps.

Example 6

Production of a Pharmaceutical Composition Using Lysine as an Excipient

To produce a first stock solution, 217.24 mg of lysine are weighed in a 25-ml volumetric flask and then dissolved in 22 ml of water for injection. 500.71 mg of the compound from Example 6A are added to the resulting solution, and the mixture is agitated for approx. 1 h until a clear solution is obtained. The pH of the resulting solution is then adjusted to pH 8 using approx. 460 μl of 1 M HCl; it is again important to avoid too sharp a local decline of the pH value and the associated precipitation of the compound from Example 6A. The volume is then topped up with water for injection purposes in order to obtain a first stock solution.

To produce a second stock solution, 242.01 mg of sodium dihydrogen phosphate are-weighed in a 50-ml volumetric flask and then dissolved in approx. 48 ml of water for injection purposes. The mixture is agitated until a clear solution is obtained. The pH of the resulting solutions is adjusted to a pH value of 8 using approx. 1.825 μl of 1 M NaOH, and the volume is then topped up with water for injection.

To produce a solution with a concentration of {8-fluoro-2-[4-(3-methoxyphenyl)piperazine-1-yl]-3-[2-methoxy-5-(trifluoromethyl)phenyl]-3,4-dihydroquinazoline-4-yl}acetic acid of 5 mg per ml of solution, 6.5 ml of the first stock solution are filled into a 25-ml volumetric flask and the volume is topped up with the second stock solution to obtain a solution with a final pH of 8.

As previously described in Example 2, for instance, pharmaceutical compositions with other concentrations of {8-fluoro-2-[4-(3-methoxyphenyl)piperazine-1-yl]-3-[2-methoxy-5-(trifluoromethyl)phenyl]-3,4-dihydroquinazoline-4-yl}acetic acid can also be produced by varying the quantity of the first stock solution.

The resulting solution is sterile filtered (pore diameter 0.22 μm) and transferred under aseptic conditions to sterile containers.

Example 7

Production of a Solid Pharmaceutical Composition which can be Reconstituted to Produce an Infusion Solution To produce a first stock solution, 261.16 mg of L-arginine are weighed in a 25-ml volumetric flask and then dissolved in 22 ml of water for injection purposes. 502.45 mg of the compound in Example 6A are added to the resulting solution, and the mixture is agitated for approx. 1 h until a clear solution is obtained. The pH of this solution is adjusted to a value of 7.8 using approx. 660 μl of 1 M HCl; it is again important that the compound from Example 6A does not precipitate. The volume is then topped up with water for injection.

To produce a second stock solution, 240.05 mg of sodium dihydrogen phosphate are weighed in a 50-ml volumetric flask and dissolved in approx. 48 ml of water for injection purposes. The mixture is agitated until a clear solution is obtained. The pH of the resulting solutions is adjusted to a value of 7.8 using approx. 1.850 μl of 1 M NaOH, and the volume is topped up with water for injection.

To produce a solution with a concentration of {8-fluoro-2-[4-(3-methoxyphenyl)piperazine-1-yl]-3-[2-methoxy-5-(trifluoromethyl)phenyl]-3,4-dihydroquinazoline-4-yl}acetic acid of 10 mg/ml, 12.5 ml of the first stock solution are placed in a 25-ml volumetric flask and the volume is topped up with the second stock solution to obtain a solution with a final pH of 7.8. One ml of the clear, colourless solutions is placed in each of 2-ml glass containers with suitable plugs and lyophilized in an EPSILON 2-4 D freeze dryer (Martin Christ GmbH, Germany) to obtain a colourless powder, which can easily be reconstituted into a solution suitable for intravenous application by adding 1 ml of water.

Example 8

Production of a Solid Pharmaceutical Composition which can be Reconstituted to Produce an Infusion Solution To produce a first stock solution, 210.49 g of L-arginine and 9665.8 g of water for injection are mixed and the mixture is agitated until a clear solution is obtained. While agitating the resulting solution, 199.23 g of the compound from Example 6A are added in small portions and the mixture is agitated for at least 30 min until a clear solution is obtained.

To produce a second stock solution, 309.19 g of sodium dihydrogen phosphate dihydrate, 827.47 g of glucose, 49.55 g of sodium chloride, and 7900.0 g of water for injection are agitated until a clear solution is obtained. The pH of the resulting solution is adjusted to 6.55 using 1 M NaOH, and 1418.29 g of water for injection purposes—less the amount of NaOH solution used to adjust the pH value—are added to the resulting solution.

To produce the desired solution, the second stock solution is added slowly and in small portions to the first stock solution while gently agitating, and the resulting solution is sterile filtered. Appropriate sterile glass containers with suitable plugs are each filled with 15 ml of the clear, colourless solution and lyophilized in a freeze dryer to obtain a colourless powder.

The lyophilisate thus obtained can be reconstituted into a solution by adding, for instance, 30 ml of water for injection purposes, and the resulting solution can then be further diluted as necessary for use in infusions.

Example 9

Production of a Second Pharmaceutical Composition Using Cyclodextrin 2.00 g of the compound from Example 6A are measured in and 30 g of a 0.1 M solution of NaOH are added. The resulting mixture is agitated for 30 min (the compound from Example 6A need not dissolve completely). 57.7 g of water for injection as well as 15.0 g hydroxypropyl-β-cyclodextrin HP5 (Kleptose HPB, Roquette) and 0.31 g of NaCl are added to the resulting mixture and agitated until a clear solution is obtained. The solution is sterile filtered (pore diameter 0.22 μm) and transferred under aseptic conditions to sterile 20-ml glass containers. The filled glass containers are sealed with infusion plugs and flange caps. The filled glass containers thus obtained may be heat-sterilized.

Example 10

Production of a Third Pharmaceutical Composition Using Cyclodextrin 2.00 g of the compound from Example 6A are measured in and 30 g of a 0.1 M solution of NaOH are added. The resulting mixture is agitated for 30 min (the compound from Example 6A need not dissolve completely). 54.8 g of water for injection purposes as well as 20.0 g hydroxypropyl-β-cyclodextrin HP5 (Kleptose HPB, Roquette) and 0.205 g of NaCl are added to the resulting mixture and agitated until a clear solution is obtained. The solution is sterile filtered (pore diameter 0.22 μm) and transferred under aseptic conditions to sterile 20-ml glass containers. The filled glass containers are sealed with infusion plugs and flange caps. The filled glass containers thus obtained may be heat-sterilized.

Example 11

Production of a Fourth Pharmaceutical Composition Using Cyclodextrin 0.5 g of the compound from Example 6A are weighed in and added to 8.75 g of a 0.1 M solution of NaOH. The resulting mixture is agitated for 30 min (the compound from Example 6A does not need to be dissolved completely). 12.45 g of water for injection purposes and 5.0 g of 2-O-methyl-β-cyclodextrin (Crysmeb, Roquette) are added to the resulting mixture and agitated until a clear solution is obtained. The pH value of the solution is adjusted to 7.5 using 1M HCl, the solution is sterile filtered (pore diameter 0.22 μm) and transferred under aseptic conditions to sterile 20-ml glass containers. The filled glass containers are sealed with infusion plugs and flange caps. The filled glass containers thus obtained may be heat-sterilized.

Example 12

Production of a Fifth Pharmaceutical Composition Using Cyclodextrin 0.5 g of the compound from Example 6A are measured in and added to 13.125 g of a 0.1 M solution of NaOH. The resulting mixture is agitated for 30 min (the compound from Example 6A does not need to be dissolved completely). 8.075 g of water for injection purposes and 5.0 g of sulphoalkyl ether-β-cyclodextrin (Captisol, CyDex Pharmaceuticals Inc.) are added to the resulting mixture and agitated until a clear solution is obtained. The pH value of the solution is adjusted to 7.5 using 500 μl of 1M HCl, the solution is sterile filtered (pore diameter 0.22 μm) and transferred under aseptic conditions to sterile 20-ml glass containers. The filled glass containers are sealed with infusion plugs and flange caps. The filled glass containers thus obtained may be heat-sterilized.

Prior to dispensing, the described solution may be diluted with an isotonic solution, e.g. an isotonic infusion solution.

C) Stability Measurement

To measure stability, the solutions produced in Examples 1 to 6 were stored for two, three and six weeks at 2-8° C., 25° C., 40° C. All solutions demonstrated adequate stability. Furthermore, the stability of a solution reconstituted from the preparation produced from Example 7 was tested over 24 h at 2-8° C., 25° C., and 40° C. The solution was demonstrated to be stable under all conditions over a period of 24 h.

D) Comparative Trials for Fixed Pharmaceutical Compositions

To demonstrate the advantageous properties of the solid pharmaceutical compositions obtained in Example 7 as compared to other solid compositions, the solid substances contained in the solution were mixed and reconstitution trials were then carried out. In none of the investigated cases it was possible to obtain a clear solution.

E) Assessment of Physiological Efficacy

The in vitro effects of the compositions according to the present invention on the replication of the HCMV (human cytomegalovirus) can be seen in the following antiviral assay:

F) HCMV Fluorescence-Reduction Test

The solution from Example 8 is used without further dilution in the test. The composition from Example 6A is used as a 50-millimolar (mM) solution in dimethyl sulphoxide (DMSO). Ganciclovir®, Foscarnet® or Cidofovir® can be used as reference compositions. One day before the beginning of the test, $1.5 \times 10^4$ human foreskin fibroblasts (NHDF cells)/well are seeded in 200 µl of cell culture medium in Wells B2-G11 of 96-well plates (black with transparent floor). The wells along the edges of each 96-well plate are filled with 200 µl of medium only in order to prevent edge effects. On the day of the test the cell culture medium in Wells B2-G11 of each 96-well plate is vacuumed off by a suction device and replaced with 100 µl of virus suspension (multiplicity of infection (MOI): 0.1-0.2). The virus used is a recombinant HCMV which has integrated an expression cassette for green fluorescence protein (GFP) in the virus genome (HCMV AD 169 RV-HG [E. M. Borst, K. Wagner, A. Binz, B. Sodeik, and M. Messerle, 2008, *J. Virol.* 82:2065-2078.]). After an incubation time of 2 h at 37° C. and 5% $CO_2$, the virus inoculate is vacuumed off by a suction device and all wells, with the exception of the wells in Column 3, are filled with 200 µl of cell culture medium. Column 2 is not treated further and serves as a virus control. The wells in Column 3 are each filled with 300 µl of composition or solution of the test substance (the latter diluted in cell culture medium) for duplicate analysis. The concentration of the respective antiviral substance in Column 3 is ~27 times as concentrated as the respective anticipated $EC_{50}$ value. The test substance in Column 3 is diluted in 8 steps to a concentration of 1:3 across the 96-well plate by transferring 100 µL from each columns into its respective right-hand column, where it is mixed with the 200 µl of cell culture medium already present there. In this way, three antiviral substances are tested in duplicate analyses. The plates are incubated for 7 days at 37° C. and 5% $CO_2$. Subsequently, all wells on the plate are washed 3 times with PBS (phosphate-buffered saline) and filled with 50 µl of PBS. The GFP intensity of each well in a 96-well plate is then determined using a fluorescence scanner (FluoBox; Bayer Technology Services GmbH; filter settings: GFP, Ex 480 nm, Em 520 nm). The measured values thus obtained can be used to determine the $EC_{50}$ of an anti-HCMV:

$EC_{50}$ (GFP-RA)=substance concentration in µM which reduces GFP fluorescence by 50% in comparison to the untreated virus control.

Representative in vitro efficacy data for the compositions according to the present invention are reproduced in Table 1:

TABLE 1

| Virus strain | Example 6A $EC_{50}$ [µM] | Example 8 $EC_{50}$ [µM] | Ganciclovir $EC_{50}$ [µM] |
|---|---|---|---|
| AD169 RV-HG | 0.0022 ± 0.0002 | 0.0026 ± 0.0005 | 2.5 ± 0.4 |

The invention claimed is:

1. A pharmaceutical composition comprising:
   a) a compound which is {8-fluoro-2-[4-(3-methoxyphenyl)piperazine-1-yl]-3-[2-methoxy-5-(trifluoromethyl)phenyl]-3,4-dihydroquinazoline-4-yl}acetic acid, wherein the carbon in position 4 of the dihydroquinazoline has a ring (S)-configuration, a salt thereof, a solvate thereof, or a solvate of a salt thereof,
   b) at least one excipient wherein said excipient is a hydroxypropyl-β-cyclodextrin, and
   c) water,
   wherein 100 ml of said composition contains:
   i) 0.5 —2.5 g {8-fluoro-2-[4-(3-methoxyphenyl)piperazine-1-yl]-3-[2-methoxy-5-(trifluoromethyl)phenyl]-3,4-dihydroquinazoline-4-yl}acetic acid, wherein the carbon in position 4 of the dihydroquinazoline ring has (S)-configuration, or a salt, a solvate or a solvate of a salt thereof, and ii) 10.0 —30.0 g of hydroxypropyl-β-cyclodextrin, wherein said composition further comprises NaOH and NaCl,
   wherein said composition is in a form suitable for intravenous administration, and
   wherein said composition has a pH in the range from 7.0 to 8.5.

2. The pharmaceutical composition according to claim 1, further comprising at least one buffer.

3. The pharmaceutical composition according to claim 2, wherein said at least one buffer is a phosphate buffer, a tris buffer, or a citrate buffer.

4. The pharmaceutical composition according to claim 1, further comprising at least one sugar.

5. The pharmaceutical composition according to claim 4, wherein said at least one sugar is glucose, sucrose, lactose, maltose, trehalose, sorbitol or mannitol.

6. The pharmaceutical composition according to claim 1, wherein the amount of said compound is up to 100 mg per ml of preparation.

7. The pharmaceutical composition according to claim 6, wherein the amount of said compound is up to 50 mg per ml of preparation.

8. The pharmaceutical composition according to claim 1, wherein said composition has a pH in the range of 7.5 to 8.5.

9. The pharmaceutical composition according to claim 1, wherein said is present in an amount of 1 to 5 equivalents in relation to the content of said compound.

10. The pharmaceutical composition according to claim 9, wherein said excipient is present in an amount of 2 to 5 equivalents in relation to the content of said compound.

11. The pharmaceutical composition according to claim 1, wherein said composition contains 1 to 10 equivalents of said at least one excipient, in relation to the content of said compound.

12. The pharmaceutical composition according to claim 1, wherein 100 ml of said composition comprises: up to 0.0 —350 mg NaOH.

13. The pharmaceutical composition according to claim 12, wherein 100 ml of said composition comprises:
   a) 1.0 —2.0 g {8-fluoro-2-[4-(3-methoxyphenyl)piperazine-1-yl]-3-[2-methoxy-5-(trifluoromethyl)phenyl]-3,4-dihydroquinazoline-4-yl}acetic acid, wherein the carbon in position 4 of the dihydroquinazoline ring has (S)-configuration, or a salt, a solvate or a solvate of a salt thereof,
   b) 12.5g —22.5 g of hydroxypropyl-β-cyclodextrin,
   c) 75 - 225 mg of NaOH,
   d) NaCl, and
   e) water.

14. A solid pharmaceutical composition produced by lyophilizing a pharmaceutical preparation according to claim 1.

15. A method for producing a pharmaceutical composition according to claim 1, said method comprising:
   A) Dissolving said excipient in water to form a solution,
   B) Adding {8-fluoro-2-[4-(3-methoxyphenyl)piperazine-1-yl]-3-[2-methoxy-5-(trifluoromethyl)phenyl]-3,4-dihydroquinazoline-4-yl}acetic acid, wherein, the carbon in position 4 of the dihydroquinazoline ring has (S)-configuration, or a salt, a solvate or a solvate of a salt thereof to said solution obtained in A),
   C) Optionally adding at least one sugar and/or buffer to said solution,
   D) Adjusting the pH of said solution to the desired value in order to obtain a pharmaceutical composition,
   E) Sterile-filtering the composition obtained in D) and filling the sterile-filtered composition into suitable containers, and
   F) Optionally performing a final sterilization of the solution obtained in
   E) under heat.

16. The method according to claim 15, further comprising lyophilizing said final solution to obtain a solid pharmaceutical composition.

17. A method for producing a pharmaceutical composition according to claim 1, said method comprising:
   I) Dissolving said excipient in water to form a solution,
   II) Adding {8-fluoro-2-[4-(3-methoxyphenyl)piperazine-1-yl]-3-[2-methoxy-5-(trifluoromethyl)phenyl]-3,4-dihydroquinazoline-4-yl}acetic acid, wherein the carbon in position 4 of the dihydroquinazoline ring has (S)-configuration, or a salt, a solvate or a solvate of a salt thereof to said solution obtained in I),
   III) Optionally adjusting the pH of the solution obtained in H) to the desired value to obtain a first solution,
   IV) Dissolving at least one sugar and/or a buffer in a part of the water to obtain a further solution,
   V) Optionally adjusting the pH of said further solution obtained in IV) to the desired value to obtain a second solution,
   VI) Mixing the first solution and the second solution to obtain a pharmaceutical composition,
   VII) Sterile-filtering the composition obtained in VI) and filling the sterile- filtered composition into suitable containers, and
   VIII) Optionally performing a final sterilization of the solution obtained in VII under heat.

18. A method for producing a pharmaceutical composition according to claim 1, said method comprising:
   a) Adding {8-fluoro-2-[4-(3-methoxyphenyl)piperazine-1-yl]-3-[2-methoxy-5-(trifluoromethyl)phenyl]-3,4-dihydroquinazoline-4-yl} acetic acid, wherein the carbon in position 4 of the dihydroquinazoline ring has (S)-configuration, or a salt, a solvate or a solvate of a salt to an aqueous NaOH solution,
   b) Adding water to the resultant solution or suspension obtained in a),
   c) Adding a hydroxypropyl-β-cyclodextrin and NaCl to the solution or suspension obtained in b), d) Sterile filtering the solution obtained in c) and filling the sterile-filtered solution into suitable containers, and e) Optionally performing a final sterilization of the solution obtained in d) under heat.

19. A method for the treatment of a cytomegalovirus infection, comprising administering a pharmaceutical composition according to claim 1 to a patient in need thereof.

20. The method according to claim 19, wherein said virus infection is a human cytomegalovirus (HCMV) infection.

21. The method according to claim 19, wherein said pharmaceutical composition is administered intravenously in an amount to provide 0.001 to 10 mg per kg of body weight of said compound.

22. The method according to claim 19, wherein said pharmaceutical composition is administered intravenously in an amount to provide 0.01 to 5 mg per kg of body weight of said compound.

23. A method for combating cytomegalovirus infections, in a human or an animal, said method comprising: administering a pharmaceutical composition according to claim 1 to said human or animal who or which requires such a treatment.

24. The pharmaceutical composition according to claim 1, wherein said composition contains up to 2.0 equivalents of NaOH, in relation to the content of said compound.

25. The pharmaceutical composition according to claim 1, wherein said excipient is present in an amount of 2 to 5 equivalents in relation to the content of said compound.

26. The pharmaceutical composition according to claim 1, wherein said excipient is present in an amount of 2.5 to 4.5 equivalents in relation to the content of said compound.

27. The pharmaceutical composition according to claim 1, wherein said excipient is present in an amount of 2 to 7 equivalents in relation to the content of said compound, and said composition contains up to 2.0 equivalents of NaOH in relation to the content of said compound.

28. The pharmaceutical composition according to claim 1, wherein said excipient is present in an amount of 2 to 7 equivalents in relation to the content of said compound, and said composition contains up to 2.0 equivalents of NaOH in relation to the content of said compound.

29. The pharmaceutical composition according to claim 1, wherein said excipient is present in an amount of 2.5 to 5 equivalents in relation to the content of said compound, and said composition contains 0.5 to 1.5 equivalents of NaOH in relation to the content of said compound.

30. The pharmaceutical composition according to claim 1, wherein said excipient is present in an amount of 2.5 to 5 equivalents in relation to the content of said compound, and said composition contains 0.75 to 0.9 equivalents of NaOH in relation to the content of said compound.

31. The pharmaceutical composition according to claim 1, wherein said compound is {(4S)-8-fluoro-2-[4-(3-methoxyphenyl)-1-piperazinyl]-3[2-methoxy-5-(trifluoromethyl)phenyl]-3,4-dihydro-4-quinazolinyl} acetic acid.

32. The pharmaceutical composition according to claim 1, wherein said excipient is hydroxypropyl-β-cyclodextrin having average number of 5 hydroxypropyl groups per cyclodextrin molecule.

33. The pharmaceutical composition according to claim 32, wherein said excipient is present in an amount of 2 to 5 equivalents in relation to the content of said compound.

34. The pharmaceutical composition according to claim 32, wherein said excipient is present in an amount of 2.5 to 4.5 equivalents in relation to the content of said compound.

35. The pharmaceutical composition according to claim 32 wherein said excipient is present in an amount of 2.5 to 5 equivalents in relation to the content of said compound, and said composition contains 0.5 to 1.5 equivalents of NaOH in relation to the content of said compound.

36. The pharmaceutical composition according to claim 32, wherein said excipient is present in an amount of 2.5 to 5 equivalents in relation to the content of said compound, and said composition contains 0.75 to 0.9 equivalents of NaOH in relation to the content of said compound.

37. The pharmaceutical composition according to claim 32, wherein said compound is {(4S)-8-fluoro-2-[4-(3-methoxyphenyl)-1-piperazinyl]-3-[2- methoxy-5-(trifluoromethyl)phenyl]-3,4-dihydro-4-quinazolinyl } acetic acid.

38. The pharmaceutical composition according to claim 32, wherein said excipient is present in an amount of 1 to 5 equivalents in relation to the content of said compound.

39. The pharmaceutical composition according to claim 38, wherein said compound is {(4S)-8-fluoro-2-[4-(3-methoxyphenyl)-1-piperazinyl]-3-[2-methoxy-5-(trifluoromethyl)phenyl]-3,4-dihydro-4-quinazolinyl} acetic acid.

40. A pharmaceutical composition comprising:
a) a compound which {8-fluoro-2-[4-(3-methoxyphenyl) piperazine-1-yl]-3-[2-methoxy-5-(trifluoromethyl)phenyl]-3,4-dihydroquinazoline-4-yl}acetic acid, wherein the carbon in position 4 of the dihydroquinazoline ring has (S)-configuration, a salt thereof, a solvate thereof, or a solvate of a salt thereof, b) at least one excipient which is a hydroxypropyl-β-cyclodextrin, and c) water, wherein 100 ml of said composition contains:
  i) 0.5 —2.5 g {8-fluoro-2-[4-(3-methoxyphenyl)piperazine-1-yl]-3-[2-methoxy-5-(trifluoromethyl)phenyl]-3,4-dihydroquinazoline-4-yl}acetic acid, wherein the carbon in position 4 of the dihydroquinazoline ring has (S)-configuration, or a salt, a solvate or a solvate of a salt thereof, and ii) 10.0 —30.0 g of hydroxypropyl-β-cyclodextrin,
wherein said composition further comprises NaOH and NaCl,
wherein said composition is in a form suitable for intravenous administration,
wherein said composition has a pH in the range from 7.0 to 8.5, and
wherein said at least one excipient is present in an amount of 1 to 10 equivalents in relation to the content of said compound, and said composition contains up to 2.0 equivalents of NaOH in relation to the content of said compound.

41. A stable liquid pharmaceutical composition comprising:
a) a compound which {8-fluoro-2-[4-(3-methoxyphenyl) piperazine-1-yl]-3-[2-methoxy-5-(trifluoromethyl)phenyl]-3,4-dihydroquinazoline-4-yl} acetic acid, wherein the carbon in position 4 of the dihydroquinazoline ring has (S)-configuration, a salt thereof, a solvate thereof, or a solvate of a salt thereof,
b) at least one excipient which is a hydroxypropyl-β-cyclodextrin, and
c) water, wherein 100 ml of said liquid pharmaceutical composition contains:
  i) 0.5 —2.5 g {8-fluoro-2-[4-(3-methoxyphenyl)piperazine-1-yl]-3-[2-methoxy-5-(trifluoromethyl)phenyl]-3,4-dihydroquinazoline-4-yl} acetic acid, wherein the carbon in position 4 of the dihydroquinazoline ring has (S)-configuration, or a salt, a solvate or a solvate of a salt thereof, and
  ii) 10.0 —30.0 g of hydroxypropyl-β-cyclodextrin, wherein said liquid pharmaceutical composition further comprises NaOH and NaCl,
wherein said liquid pharmaceutical composition has a pH in the range from 7.0 to 8.5,
wherein said liquid pharmaceutical composition is in the form of a solution, and
when stored at a temperature of 2 ° C. to 8 ° C. for a storage period of at least two weeks, or at 25 ° C. for a storage period of at least two weeks, or at 40 ° C. for a storage period of at least two weeks, said solution retains a minimum proportion of >90% {8-fluoro-2-[4-(3-methoxyphenyl)piperazine-1-yl]-3-[2-methoxy-5-(trifluoromethyl)phenyl]-3,4-dihydroquinazoline-4-yl}acetic acid in solution.

42. A stable liquid pharmaceutical composition comprising:
a) a compound which {8-fluoro-2-[4-(3-methoxyphenyl) piperazine-1-yl]-3-[2-methoxy-5-(trifluoromethyl)phenyl]-3,4-dihydroquinazoline-4-yl}acetic acid, wherein the carbon in position 4 of the dihydroquinazoline ring has (S)-configuration, a salt thereof, a solvate thereof, or a solvate of a salt thereof, b) at least one excipient which is a hydroxypropyl-β-cyclodextrin, and c) water, wherein 100 ml of said liquid pharmaceutical composition contains:
  i) 0.5 —2.5 g {8-fluoro-2-[4-(3-methoxyphenyl)piperazine-1-yl]-3-[2-methoxy-5-(trifluoromethyl)phenyl]-3,4-dihydroquinazoline-4-yl}acetic acid, wherein the carbon in position 4 of the dihydroquinazoline ring has (S)-configuration, or a salt, a solvate or a solvate of a salt thereof, and ii) 10.0 —30.0 g of hydroxypropyl-β-cyclodextrin, wherein said liquid pharmaceutical composition further comprises NaOH and NaCl, wherein said liquid pharmaceutical composition has a pH in the range from 7.0 to 8.5, wherein said liquid pharmaceutical composition is in the form of a solution and wherein, after said having been diluted or reconstituted to a final concentration of 0.8-10 mg of said compound per ml for infusion at 2 ° C. to 8 ° C., said solution retains a minimum proportion of >90% {8-fluoro-2-[4-(3-methoxyphenyl)piperazine-1-yl]-3-[2-methoxy-5-(trifluoromethyl)phenyl]-3,4-dihydroquinazoline-4-yl}acetic acid in solution for a period of at least four hours.

43. The stable liquid pharmaceutical composition according to claim 42, wherein said compound is is {(4S)-8-fluoro-2-[4-(3-methoxyphenyl)-1-piperazinyl]-3-[2- methoxy-5-(trifluoromethyl)phenyl]-3,4-dihydro-4-quinazolinyl} acetic acid.

44. The stable liquid pharmaceutical composition according to claim 41, wherein said compound is {(4S)-8-fluoro-2-[4-(3-methoxyphenyl)-1-piperazinyl]-3-[2-methoxy-5-(trifluoromethyl)phenyl]-3,4-dihydro-4-quinazolinyl} acetic acid.

* * * * *

UNITED STATES PATENT AND TRADEMARK OFFICE
CERTIFICATE OF CORRECTION

PATENT NO. : 10,603,384 B2
APPLICATION NO. : 14/381290
DATED : March 31, 2020
INVENTOR(S) : Paulus et al.

Page 1 of 1

It is certified that error appears in the above-identified patent and that said Letters Patent is hereby corrected as shown below:

On the Title Page

Item (73) Assignee: reads -- AICURIS GMBH & CO., KG --
Should read: -- AICURIS ANTI-INFECTIVE CURES GMBH --.

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*